US009683957B2

(12) United States Patent
Mwakikunga

(10) Patent No.: US 9,683,957 B2
(45) Date of Patent: Jun. 20, 2017

(54) FIELD EFFECT TRANSISTOR AND A GAS DETECTOR INCLUDING A PLURALITY OF FIELD EFFECT TRANSISTORS

(71) Applicant: CSIR, Brummeria, Pretoria (ZA)

(72) Inventor: Bonex Wakufwa Mwakikunga, Pretoria (ZA)

(73) Assignee: CSIR, Brummeria, Pretoria (ZA)

(\*) Notice: Subject to any disclaimer, the term of this patent is extended or adjusted under 35 U.S.C. 154(b) by 0 days.

(21) Appl. No.: 14/894,460

(22) PCT Filed: May 26, 2014

(86) PCT No.: PCT/IB2014/061713
§ 371 (c)(1),
(2) Date: Nov. 27, 2015

(87) PCT Pub. No.: WO2014/191892
PCT Pub. Date: Dec. 4, 2014

(65) Prior Publication Data
US 2016/0116434 A1    Apr. 28, 2016

(30) Foreign Application Priority Data

May 29, 2013  (ZA) .................................. 2013/03911

(51) Int. Cl.
*H01L 29/49*     (2006.01)
*G01N 27/414*    (2006.01)

(52) U.S. Cl.
CPC ..... *G01N 27/4141* (2013.01); *G01N 27/4146* (2013.01)

(58) Field of Classification Search
CPC . G01N 27/127; G01N 33/004; G01N 33/0037
See application file for complete search history.

(56) References Cited

U.S. PATENT DOCUMENTS 7,948,041 B2     5/2011  Bryant et al.
2014/0103335 A1*  4/2014  Yamazaki ........... H01L 29/7869
                                            257/43

OTHER PUBLICATIONS

International Search Report mailed Sep. 7, 2014; PCT/IB2014/061713.

\* cited by examiner

*Primary Examiner* — Michael Shingleton
(74) *Attorney, Agent, or Firm* — Ladas & Parry LLP

(57) ABSTRACT

A field effect transistor comprising a source including a plurality of electrode projections with spaces in between. A drain includes a plurality of electrode projections each located in one of the spaces between the electrode projections of the source thereby forming a drain-source electrode connection area of alternating drain and source projections. A gate is spaced apart from the drain-source electrode area thereby forming a channel between the gate and the drain-source electrode connection area wherein the gate runs parallel to the channel. A plurality of nano-structures is located in the drain-source electrode area thereby to form an electrical connection between the electrode projections of the drain and source in the drain-source electrode connection area. The invention extends to a gas detector including a plurality of field effect transistors as described above located on a substrate.

8 Claims, 12 Drawing Sheets

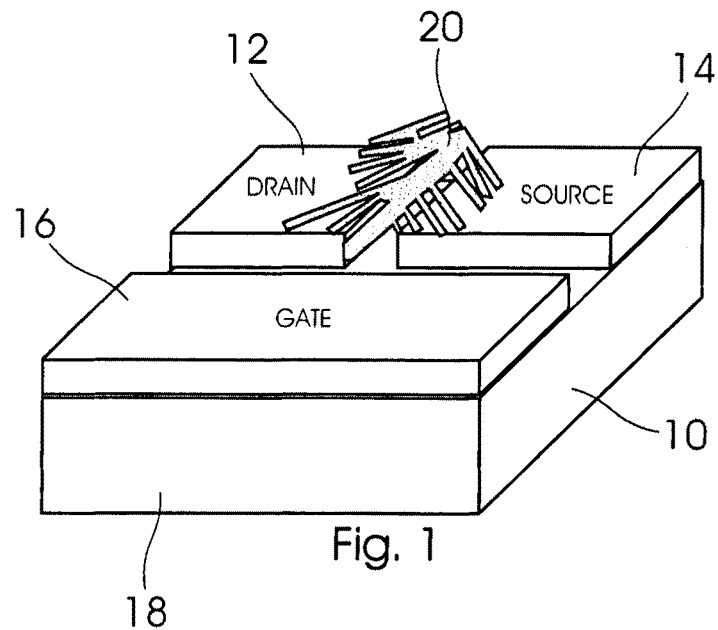
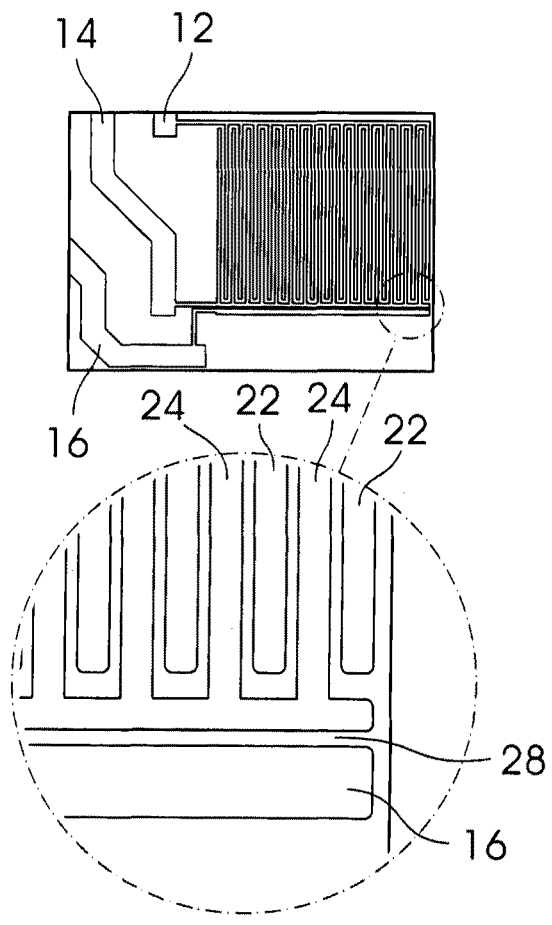
Fig. 1
Fig. 2

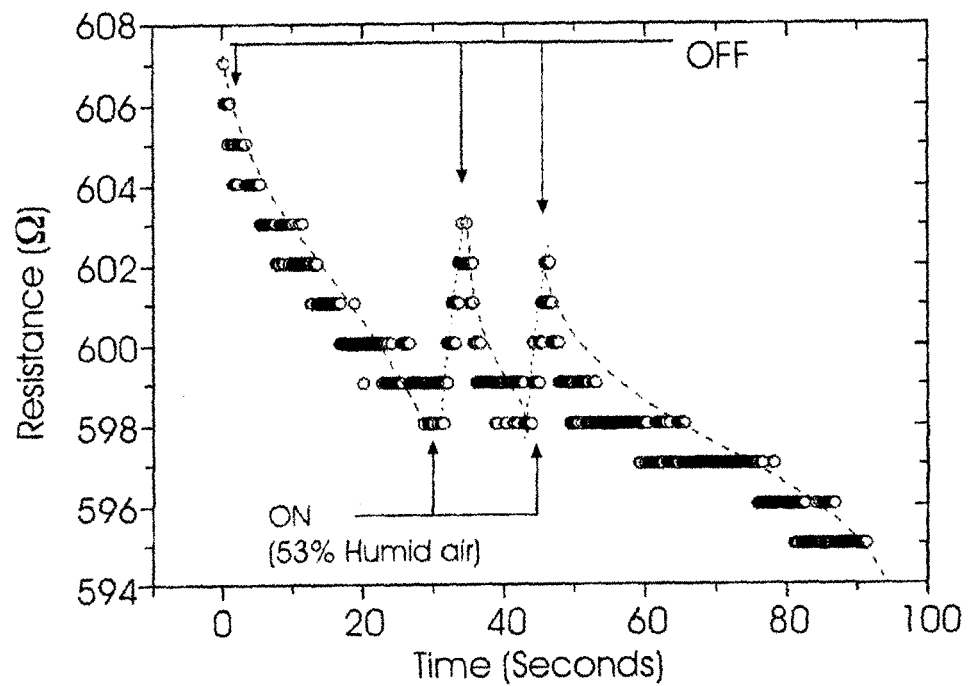
Fig. 11
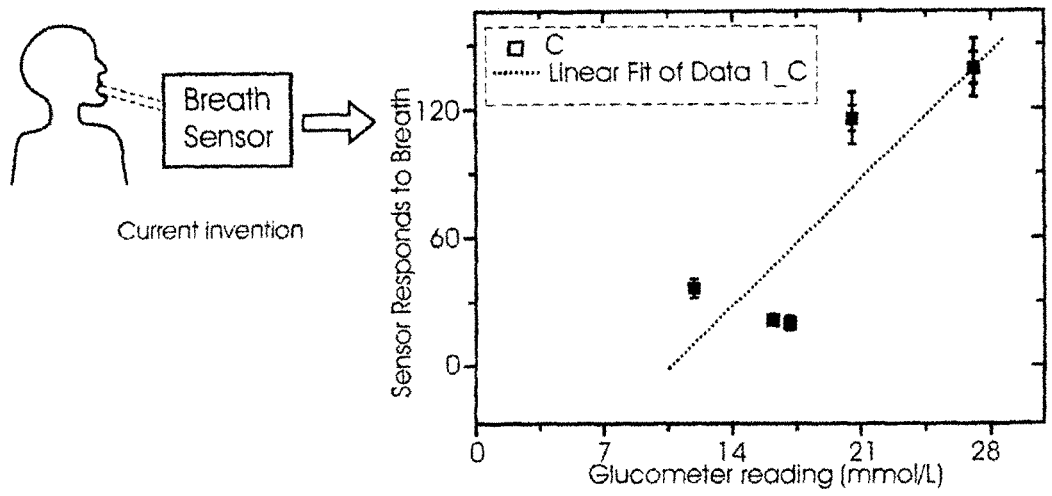
Fig. 12
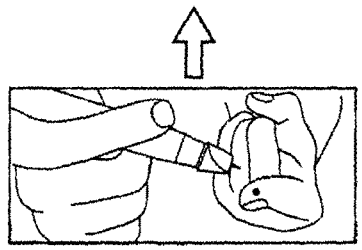

FIELD EFFECT TRANSISTOR AND A GAS DETECTOR INCLUDING A PLURALITY OF FIELD EFFECT TRANSISTORS

BACKGROUND OF THE INVENTION

This patent application relates to a field effect transistor and a gas detector including a plurality of field effect transistors.

Field effect transistors (FET) are well known and include three terminals being a source, drain and gate. There are many different types of FETs with various structures and methods of fabrication.

In terms of gas sensors, traditional gas sensor devices based on semiconductor materials employ two terminals to measure impedance of the material when in the presence or absence of gases.

In order to enhance the sensitivity as well as gas-specificity, such devices have to be heated at moderately high temperatures.

However, heating not only limits large-scale integration in small micro-chips but also is a major cost which hinders the operation and demands highly on battery life.

The present invention seeks to provide an improved FET structure together with an application for the improved FET in an improved gas detector.

SUMMARY OF THE INVENTION

According to a first aspect of the invention there is provided a field effect transistor comprising:
  a source including a plurality of electrode projections with spaces in between;
  a drain including a plurality of electrode projections each located in one of the spaces between the electrode projections of the source thereby forming a drain-source electrode connection area of alternating drain and source projections;
  a gate spaced apart from the drain-source electrode area thereby forming a channel between the gate and the drain-source electrode connection area wherein the gate runs parallel to the channel; and
  a plurality of nano-structures located in the drain-source electrode area thereby to form an electrical connection between the electrode projections of the drain and source in the drain-source electrode connection area.

The drain, source and the gate are preferably in the same plane.

The electrode projections of the drain may be elongate in shape and connected at or near one of their ends.

The electrode projections of the source may be elongate in shape and connected at or near one of their ends.

The plurality of nano-structures located in the drain-source electrode area are positioned randomly on the drain-source electrode area.

The drain-source electrode connection area is approximately 90 micron by 90 micron.

According to a second aspect of the invention there is provided a gas detector including a plurality of field effect transistors located on a substrate, each of the field effect transistors including:
  a source including a plurality of electrode projections with spaces in between;
  a drain including a plurality of electrode projections each located in one of the spaces between the electrode projections of the source thereby forming a drain-source electrode connection area of alternating drain and source projections;
  a gate spaced apart from the drain-source electrode area thereby forming a channel between the gate and the drain-source electrode connection area wherein the gate runs parallel to the channel; and
  a plurality of nano-structures located in the drain-source electrode area thereby to form an electrical connection between the electrode projections of the drain and source in the drain-source electrode connection area.

The gas detector may include eight field effect transistors located on a substrate.

The gas detector may include a processor to receive signals from each of the field effect transistors and to process the signals to determine the presence of one or more gases.

BRIEF DESCRIPTION OF THE DRAWINGS

FIG. 1 shows a schematic drawing of a field effect transistor (FET) in accordance with an example embodiment;

FIG. 2 shows a more detailed schematic drawing of the FET of FIG. 1, particularly showing the source, drain and gate areas in greater detail;

FIG. 11 shows the resistance across a multiwall carbon nano-tube in time as it was exposed to humid air;

FIG. 12 shows an example application of the present invention in the detection of acetone in diabetic patient breath correlated to the blood sugar levels;

DESCRIPTION OF PREFERRED EMBODIMENTS

Figure 3:
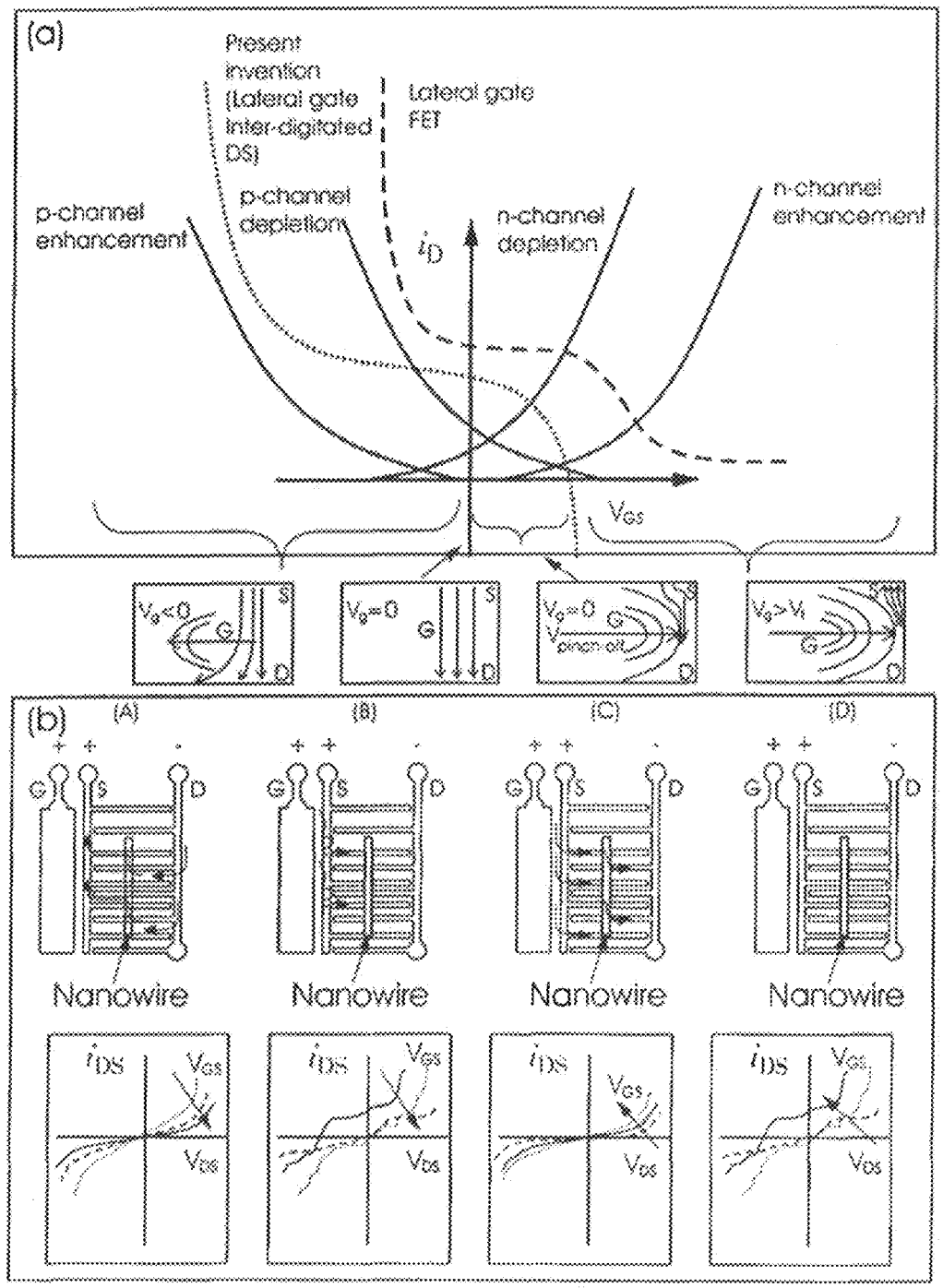
FIG. 3(a) shows four main scenarios of the mechanisms of the effect of the gate voltage (Vg) on the source to drain current (Ids) of the FET illustrated above when the drain-source voltage, VDS, is constant, (b) are the schematics of the four main ways (A, B, C and D) of connecting the gate terminal positive or negative relative to the drain-source polarities illustrating the fact that in this new kind of transistor two configurations lead to smooth output characteristics and the other two lead to random and disordered output characteristics.

In the following description, for purposes of explanation, numerous specific details are set forth in order to provide a thorough understanding of an embodiment of the present disclosure. It will be evident, however, to one skilled in the art that the present disclosure may be practiced without these specific details.

Referring to the accompanying Figures, an example field effect transistor (FET) 10 is illustrated.

The FET 10 includes a drain 12, a source 14 and a gate 16 all located on a base 18.

Connecting the drain 12 and the source 14 are a plurality of nano structures 20 which will be described in more detail below.

Referring to FIG. 2, the source 14 includes a plurality of electrode projections 24 with spaces in between as illustrated.

The electrode projections of the source 14 may be elongate in shape and connected at or near one of their ends.

The drain 12 also includes a plurality of electrode projections 22 each located in one of the spaces between the electrode projections of the source thereby forming a drain-source electrode connection area 26 of alternating drain and source projections.

The electrode projections of the drain 12 may be elongate in shape and connected at or near one of their ends.

This forms a drain-source electrode connection area 26 including interdigitated electrode projections 24 and 26 that are interlocked like the fingers of clasped hands.

The gate 16 is spaced apart from the drain-source electrode area 26 thereby forming a channel 28 between the gate and the drain-source electrode connection area 26 so that the gate 16 runs parallel to the channel 28.

It will be appreciated that the gate 16 rests in the same surface plane as the drain 12 and the source 14 but does not touch the drain 12 or the source 14.

It will be appreciated that the drain 12, source 14 and the gate 16 are in the same plane.

A plurality of nano-structures 20 are located in the drain-source electrode area 26 thereby to form an electrical connection between the electrode projections of the drain and source in the drain-source electrode connection area. These are schematically represented in FIG. 1 and will be described in more detail below.

In a prototype embodiment, the FET 10 was manufactured as follows.

First the base 18 is formed from alumina square substrates. These are then coated with a metal film, preferably gold, by d.c. sputtering.

The gold film is scribed with a T-shaped groove by means of a diamond knife whose tip is typically 30-60 micrometers. The scribing is made to ensure that the gold film is completely dug out in the areas desired to be insulated in such a way that only the parts of the film designated to be the drain, the source and the gate are left as-coated with gold.

It will be appreciated that this technique is simple when compared to the complexity and costs of accomplishing the same task in a standard clean room facility.

On-chip growth of three different types of one dimensionally nano-structured material (TiO$_2$ nano-fibres, V$_2$O$_5$ nano-fibres, SnO$_2$ nanowires and ZnO nano-rods) can be carried out by different techniques, for example: (1) electrospinning (2) chemical vapor deposition and (3) hydrothermal synthesis. This forms the nano-structures 20.

Thus, gold contacts in the form of interdigitated electrodes, printed on an area of 90 microns by 90 micron, form the drain and source terminal. A third electrode is placed parallel and in the same plane as the drain-source area. Only when the nano-materials are placed on the drain-source area, does the device become a transistor. This kind of transistor can be called the lateral gate interdigitated drain-source FET (LGIDSFET). An illustration is given in FIG. 2. Such eight transistors are arranged in an array on 1 mm by 1 mm Si/SiO$_2$ wafer and each electrode is wire bonded on the each of the 24 pins of a chip carrier as will be explained further below.

For a FET 10 to be used in a gas detector, as will be described in more detail below, the FET 10 was manufactured with either of two nano-materials to make the nano-structures 20.

These two nano-materials were VO$_2$/V$_2$O$_5$ core-shell nano-ribbons and multi-wall carbon nano-tubes.

In order to accomplish this, a suspension of VO$_2$/V$_2$O$_5$ nano-ribbons or multi-wall carbon nano-tubes in isopropanol liquid is formed.

In one example, the suspension of VO$_2$/V$_2$O$_5$ core-shell nano-ribbons in isopropanol is prepared by weighing 5, 3, 1, 0.5, 0.2 mg of VO$_2$/V$_2$O$_5$ core-shell nano-ribbons and transferring the powder into 100 mL of isopropanol tube. Similarly 5, 3, 1, 0.5, 0.4, 0.2 mg of carbon nano-tubes can be released into 100 mL of isopropanol liquid.

The suspension is placed in an ultrasonic bath for 5 minutes in order for the nano-structures to be shaken and dispersed into the liquid evenly.

After several tests, it was found that, for VO$_2$/V$_2$O$_5$ core-shell nano-ribbons, the most optimum concentration was 1 mg/100 mL whereas it was 0.4 mg/100 mL for carbon nanotubes Once the suspensions have been prepared, micro-liter droplets were transferred using a dropper onto the FET in the area 26 containing the drain source electrodes.

Figure 4:
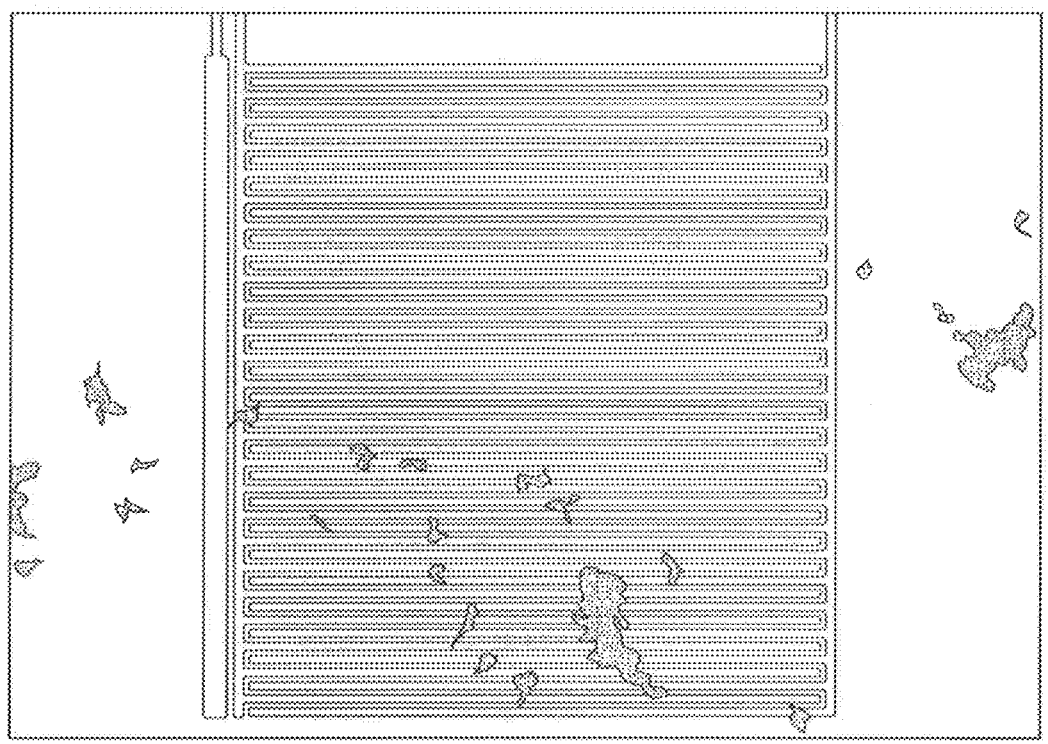
FIG. 4 shows an illustration of how nano-ribbons of VO2 spread throughout the inter-digitated drain source area.

After drop casting the nanostructures, scanning electron microscopy is performed to be sure that the nanostructures are in place. FIG. 4 is a SEM image showing how VO$_2$/V$_2$O$_5$ core-shell nano-ribbons are spread out on the drain-source area 26.

As can be seen, the nano-particles placed on the interdigitated contacts between the drain electrodes and the source electrodes fall randomly in such a way that the drain-source channel in the nano-particles or nano-wires orients at random angles with the gate direction. This arrangement offers much more degrees of freedom of the interaction between the electric field in the gate and the electron current in the drain and source which has not been possible previously.

In traditional transistors, the nano-structure mostly runs perpendicular to the gate terminal. In this situation the drain current is given by the Shockely's equation for a MOSFET:

$$I_{DS} = \frac{W}{L} C (V_G - V_T)^2; \quad C = \frac{2\pi\varepsilon\varepsilon_0 L}{\ln(2h/r)} \qquad (1)$$

And for junction FET (JFET) we have:

$$I_D = \frac{qN_D\mu_D W_D}{L}\left[V_{DS} - \frac{2[(V_{DS}+V_T-V_{GS})^{3/2}-(V_T-V_{GS})^{3/2}]}{3V_{p0}^{1/2}}\right] \quad (2)$$

where W and L correspond to the channel diameter and length respectively and C is the gate dielectric capacitance per unit length, r=L/2 is the radius of the channel, h is the thickness of the dielectric and the rest of the symbols carry the usual meanings. By placing one-dimensional nano-structures such as nano-wires, nano-rods and nanotubes on the drain-source area in this invention, any angle between the gate electrode and the nano-structure is possible in such a way that a new equation different from the Shockley's equation has to be determined. From the first empirical results on this invention, it has become clear that there are two possibilities viz: (1) the cubic law rather than the Shockely's square law is preferred thus:

$$I_{DS}=\alpha_0+\alpha_1 V_G+\alpha_2 V_G^2+\alpha_3 V_G^3 \quad (3)$$

where the value and polarity of the coefficients $\alpha_0$, $\alpha_1$, $\alpha_2$ and $\alpha_3$ have to be determined for a specific gas interacting with a particular sensing nano-material after fitting equation 2 to experimental data from the currently invented microchip.

or (2) for reverse bias: since the ID vs VGS shows the opposite of the Shockley equation, one can adopt the exponential decay equation. In the forward bias, the ID vs VGS again shows the opposite profile of the Shockley equation. Here we may adopt the negative of Equation 1. The sum of the both the forward and reverse bias equations lead to $$I_{DS} = A\exp\left(-\alpha\frac{eV_{GS}}{k_BT}\right) - \beta\frac{WC}{L}(V_T-V_{GS})^2 \quad (4)$$

It shall be noted that when the differential $\partial I_{DS}/\partial V_{GS}$ (or transconductance $g_m$) is performed on Equation 1 to Equation 3, only Equation 3 (pertaining to the present invention) yields a differential that, when plotted with $V_{GS}$ on the ordinate axis, displays a hump at a characteristic value of $V_{GS}$. Gate voltage dependent response, $\Re(V_{GS})$ of this transistor, when it is applied in sensing, can be obtained from the differential of Equation 3 and 4 as follows:

$$\Re(V_{GS}) = \frac{1}{g_{m0}}\left(\frac{\partial I_{DS}}{\partial V_{GS}}\right)\bigg|_{V_{DS}} = \frac{1}{g_{m0}}[\alpha_1+\alpha_2(V_{GS}-V_T)+\alpha_3(V_{GS}-V_T)^2] \quad (5)$$

$$\Re(V_{GS}) = \frac{1}{g_{m0}}\left(\frac{\partial I_{DS}}{\partial V_{GS}}\right)\bigg|_{V_{DS}} = -\alpha\frac{e}{k_BT}A\exp\left(-\alpha\frac{eV_{GS}}{k_BT}\right) - 2\beta\frac{WC}{L}(V_{GS}-V_T) \quad (6)$$

This type of analysis on this kind of transistor sensor is one unique characteristic that will aid in the ability to distinguish one gas environment from the other by simply "tuning" to the desired stimulus by the gate voltage of the transistor sensor, as will be shown in the next sections.

There is also an interesting effect of the electric field in the gate on the drain-source current in the nano-structures placed in the drain-source area that, it is possible, as given in the illustration in FIG. 3(a) that when the gate voltage exceeds the threshold voltage ($V_T$), the current from the source to drain reverts back to the source.

This has not been observed in any kind of transistor. In traditional transistor, the drain-source current only tends to "pinch-off" but does flow in the negative direction. This new property may be related to the Gunn effect where the current experiences a decrease and hence the differential with voltage becomes negative conductance. In the present invention the current actually flows in the opposite direction. Thus when $V_g<0$, $I_{ds}$ is considerably large as the negative $V_g$ causes the Ids flow to spread out which is not the case when $V_g=0$. When $V_g>0$, the current continues to drop until $V_g$ reaches $V_{pinch-off}$ when $I_{ds}$ is stopped. The gate voltage that causes zero current is sometimes referred to as threshold voltage or $V_T$. When $V_g$ goes higher than $V_T$, the transistor shows a reversal in the $I_{ds}$.

Another new feature of this new transistor, owing to its geometry is the four main ways of connecting the gate as either positive or negative relative to the polarity of drain-source current. The polarity of the drain-source has an effect on the output characteristics of the LGIDSFET. In FIG. 3(b) a schematic is given where the polarities of D and S are swapped when G is either + or − and output characteristics are smooth or random. It is smooth when the polarity of the source is the same polarity of the gate and random when the polarities are opposing.

Figure 5:
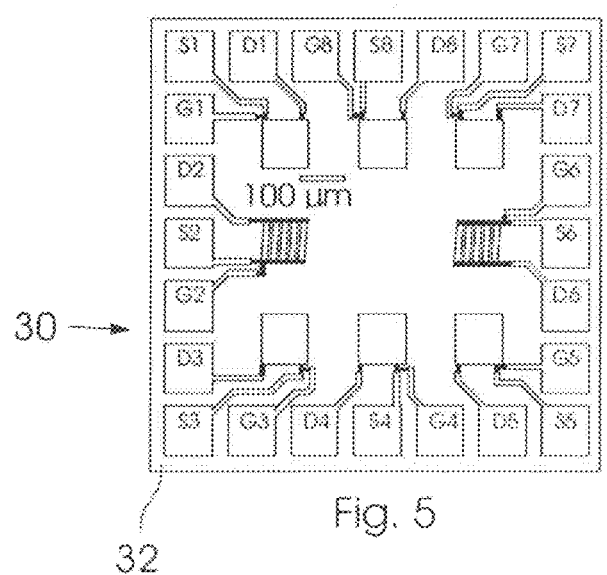
FIG. 5 shows a schematic drawing of a gas detector using a plurality of the FETs shown in FIGS. 1 and 2, in accordance with an example embodiment.
Figure 6:
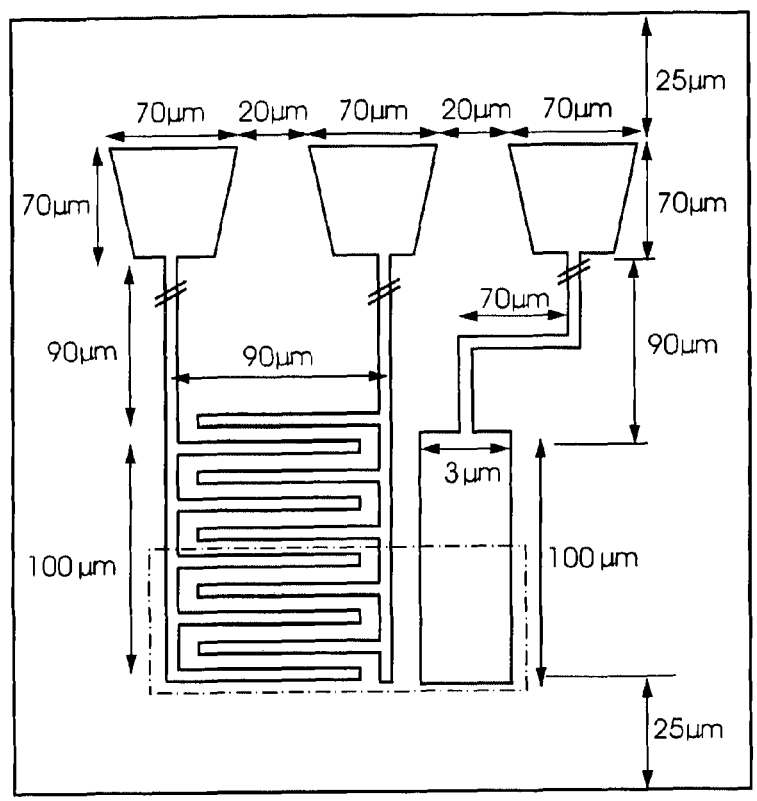
FIG. 6 shows another schematic drawing of one of the FETs of the gas detector shown in FIG. 5.
Figure 6:
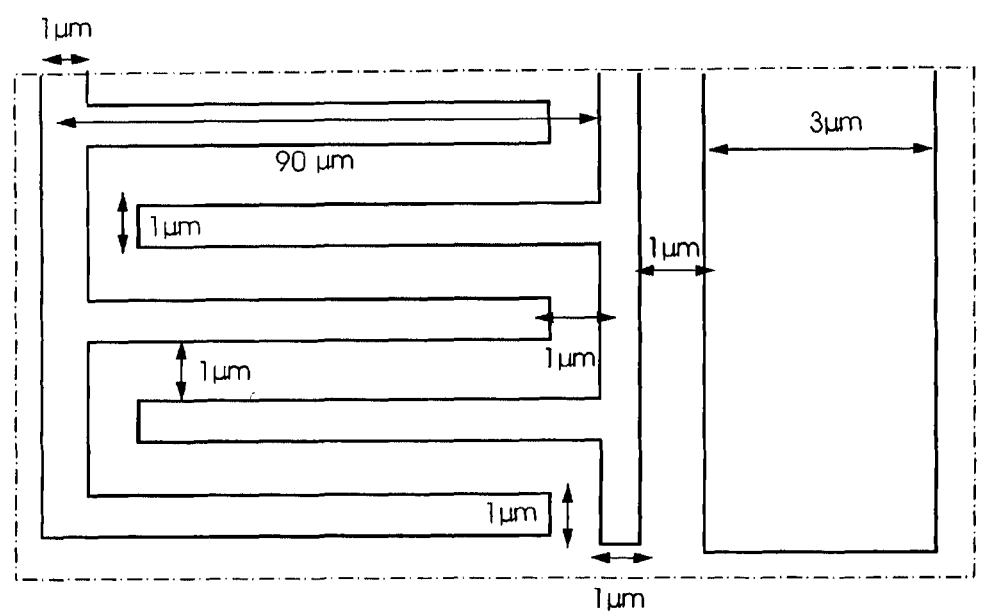
Figure 7:
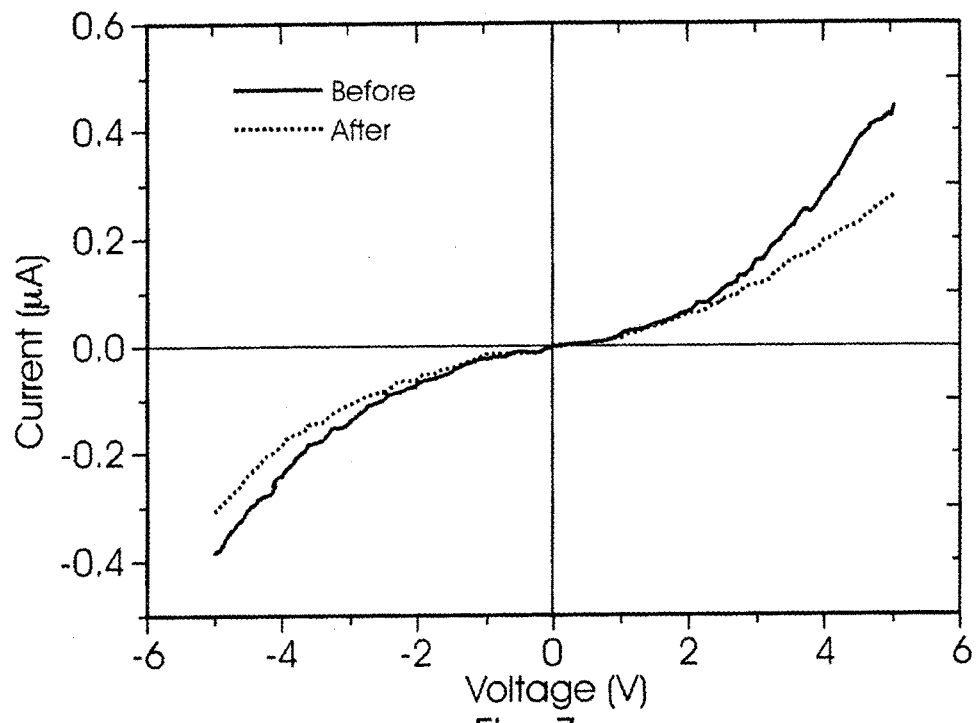
FIG. 7 shows forward current-voltage characteristics for VO2/V2O5 core-shell nano-ribbons in normal conditions and after being exposed to humid air showing the conductance decreases upon exposure to humid air and the influence of the gate voltage on the drain (output current)

The FET 10 described above was used to create a gas detector 30 as illustrated in FIGS. 5 and 6.

In the illustrated embodiment, a plurality of the FETs 10 are used to form the gas detector. The prototype embodiment included eight FETs 10 but it will be appreciated that this number may differ depending on the application required.

The eight FET platform was manufactured as follows.

On a 1000 um by 1000 um Si/SiO2 substrate 32, eight FET components 10 are placed, each having three gold terminals shown as s1;d1;g1, s2;d2;g2 and so forth. A space of 25 um was left all around the substrate.

Each component measures 250 um by 25 um, with a spacing of 100 um in between them.

Each of the three gold terminals measure 70 um by 70 um. A spacing of 20 um is given between the terminals. Two out of the three gold terminals are connected to the 'finger' interdigitated features via 30 um long gold strips. These strips are 1 um in width.

The third gold terminal leads via a 70 um bend to a gold plate measuring 100 um by 3 um and placed 1 um away from the inter-digitated finger features.

The main high-ways of the finger features are 90 um apart. The interdigitated fingers are 1 um in width but one finger connected to one high-way leaves a 1 um space on the opposite highway and in between the neighboring fingers and so on. With a pitch of 1 um between the finger digits and the interdigitated area measuring 100 um in length leads to about 100 digitations (50 fingers from each of the two highways).

An initial sensing test is to check the current-voltage (I-V) characteristics of the drain-source area after the $VO_2/V_2O_5$ nano-ribbons or carbon nanotubes are placed.

It should be noted that it is possible to place different nano-structures at each FET platform especially those nano-structures that are suited to sense a particular and specific gas.

However, a common problem in nano-scale sensors is that nano-scale sensors have high sensitivity but have low selectivity and so one alternative is to place the same kind of nano-structures at all locations on the micro-chip. Selectivity of each FET to a particular gas can be accomplished by varying the gate voltage bias at each FET. This will be described in more detail below.

In any event, this test is carried in order to ascertain that the chip feature size of 1 um establishes electrical connections to the nano-structures.

After establishing that the contacts are secure, transient resistance/conductance on the drain-source is determined and recorded via chart recorder software.

Transient resistance/conductance plots, that is to say, resistance/conductance versus time plots, are used to determine response $S_{res}$, recovery $S_{rec}$, response time, $\tau_{res}$, recovery time, $\tau_{rec}$, defined respectively in the following paragraphs.

When deciding which materials are to be employed as sensors of a particular gas, it is important to assess the range of materials based on a valid yardstick. The following figures of merit have been used extensively to assess sensors. These are more comprehensively described in the list of references 1-10 cited below in appendix A:

(a) Response, $S_{res}$, (the relative change in resistance of a material in presence or absence of a gas). In order to study the response, for instance, there are two major definitions in literature: either $S=|R_{in}-R_{out}|R_{in}$ or simply $S=R_{out}/R_{in}$ where $R_{in}$ is the resistance of the sensor material when in presence of the analyte gas and $R_{out}$ is the resistance in the absence of such a gas. Response as function of temperature was already derived by the inventor to take the form of $S(T)=(R_{in}/R_{out}) \exp((E_a-E_{0in})/k_BT))$ or $S(T)=1-(R_{in}/R_{out}) \exp((E_a-E_{0in})/k_BT))$ where $E_a$ and $E_{0in}$ are the activation energies of the sensor material in the absence and presence of the analyte gas respectively and $k_B$ is the Boltzmann constant. This equation suggests that response increases (decreases) as temperature is increased when $E_a > E_{0in}$ ($E_a < E_{0in}$), that is, when the analyte-sensor interaction is oxidative (reductive).

(b) Recovery, $S_{rec}$, the relative change in resistance from when the sensor is fully exposed to the analyte and when the stimulus is fully removed.

(c) Selectivity (the ability of a material to respond to that particular gas and not to other gas types present).

(d) Response time, $\tau_{res}$, which is the period of time, tres taken for the resistance to change ($|R_{in}-R_{out}|$) to 90% of the original resistance or by one-order of magnitude.

(e) Recovery time, $\tau_{rec}$, the time taken for the resistance to return to 90% of the original resistance or by one-order of magnitude to the original resistance after sensing).

Other parameters that important in deciding the performance of the sensors are:

(f) Working temperature, $T_{opt}$, which is the temperature at which the sensor material must be heated up to in order to get the most optimum response (g) Relative humidity of the surroundings (H).

(h) Atmospheric pressure ($p_{atm}$).

It was found in the prototype that for a $VO_2/V_2O_5$ system, the response time is typically about 5 seconds but the recovery time is much longer which is typical of nano-structures. This drawback can be address by introducing a pulse in the gate and the sensor is refreshed again.

However, it has been found that the resistance-time profile of multiwall carbon nano-tube have a faster response with the response time of lower than 3 seconds and much more rapid recovery at 7 seconds. Thus there is no need of a gate refreshing or UV light activation.

Figure 14:
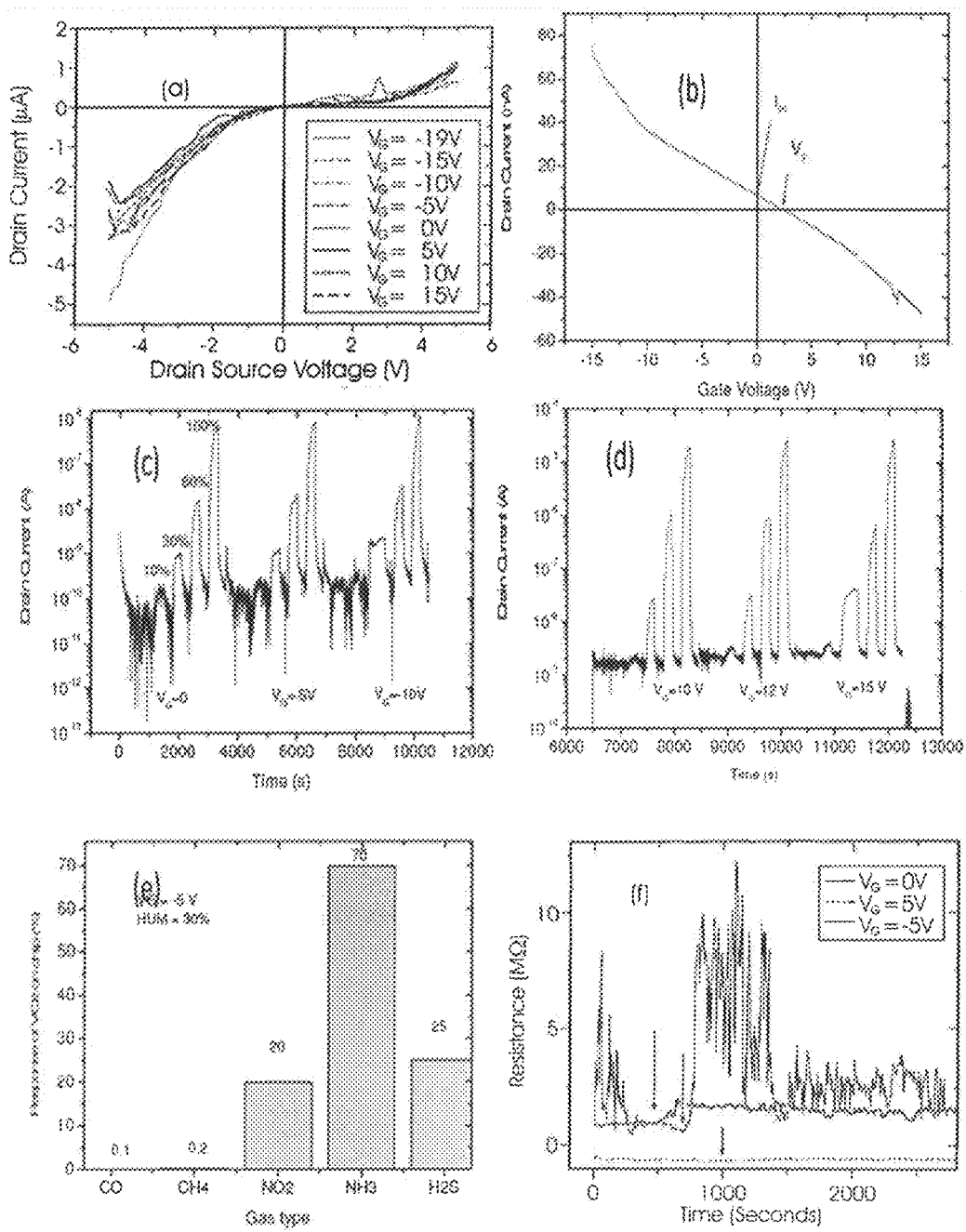
FIG. 14 shows forward current-voltage characteristics for VO2/V2O5 core-shell nano-ribbons.

It should also be highlighted that response times and recovery times are affected by the gate voltage ($V_{GS}$). This is illustrated in FIG. 14(*f*) where one can observe that recovery times is 20 minutes when $V_{GS}=0$ but become much shorter (about 1 minute) when bias voltage becomes −5V.

In order to pursue how selectivity, as in definition (c) above, gate voltages are varies and corresponding drain-sources are taken before and after exposure to various gases. In the prototype of the present invention it was found that the drain current decreases as one sweeps the gate voltage from negative voltage to positive. This is different from normal back-gate transistors where the drain current increases as one increases the gate voltage. In the positive gate voltage, the drain current drastically drops to a "pinch-off" state. Each gas environment gives a unique pinch-off voltage or threshold voltage $V_T$. This property helps in calibrating each of the eight sensors on this chip to a specific gas (FIG. 11).

A plot of drain current against gate voltage when the chip is in normal air and when under the influence of humid air shows a downward trend to a drain current of zero where the threshold voltage value, $V_T$, depends on the environment surrounding the sensor. This trend shows that each gas environment has its unique $V_T$.

Materials with the highest response are ideal but it would be futile if this high response is only achieved at extremely low or high temperatures in which case it will be energy expensive to operate such a sensor device. A good sensor should have high response at room temperature even in relatively high humidity conditions. These characteristics are necessitated by the increasing demand for long battery lifetime. If the sensor has to be heated above or cooled below room temperature, the demand on battery power becomes enormous and the sensor cannot operate for a long enough time. Operation at room temperature avoids this extra heating or cooling. In addition, a good sensor must have a very short response time to the analyte gas as well as a rapid recovery when the analyte gas is removed. Response and recovery times are in turn temperature dependent. All these good qualities are difficult to get out of a single material.

With the present invention, one gets closer to getting all the good qualities of any single sensing material.

The inventor and collaborators have published a method of assessing several sensing materials on the above properties. The method uses some mathematical formulae which united sensor response $S_{res}$, sensor recovery $S_{rec}$, response and recovery times ($\tau_{res}$, $\tau_{rec}$), temperature T, atmospheric pressure p, humidity H. The equation for how efficient any sensing material can be is given as:

$$\eta^*_{eff}(T) = \frac{S_{res} \cdot S_{rec} \exp\left(-\frac{(T-T_{opt})^2}{2\sigma_{SD}^2}\right) \exp\left[-\left(\frac{\frac{T_{room}}{T}+\frac{H}{H_{std}}-\frac{p}{p_{std}}-}{\frac{1 \sec}{\tau_{res}}-\frac{1 \sec}{\tau_{rec}}}\right)\right]}{S_{res}(T_{room}) \cdot S_{rec}(T_{room}) \exp\left(-\frac{(T_{room}-T_{opt})^2}{\sigma_{SD}^2}\right)} \times 100\% \quad (7)$$

In this recent publication, the materials were contacted as powders. The method was very crude in that the modes of contacts were not the same for all materials considered.

In order to illustrate the present invention, one gives all the parameters obtained by the crude method in Table 1 (where CoP stands for coefficient of performance which is different from sensing efficiency) and compares this with the properties for the same two materials tested so far—$VO_2$ and Carbon nanotubes—on the invented microchip. This means that by employing the new invention, one gets great performance improvements.

| Method of testing | Material | T (° C.) | $t_{res}$ | $t_{rec}$ | $S_{res}$ | $S_{rec}$ | CoP | $CoP_{ideal}$ | $\eta(\%)$ |
|---|---|---|---|---|---|---|---|---|---|
| Traditional | VO2 NRds | 24 | 1464 | 239 | 0.05 | 0.09 | $1.87 \cdot 10^{-2}$ | 0.05 | 36.5 |
| Present Invention | VO2 NRds | 24 | 5 | 120 | 2.00 | 1.00 | 0.24 | 0.51 | 47.5 |
| Traditional | SnO2:CNT NPs | 50 | 455.8 | 31.8 | 1.28 | 0.43 | $2.5 \cdot 10^{-1}$ | 0.63 | 8.5 |
| Present Invention | CNT | 24 | 3 | 7 | 0.0067 | 0.0067 | 0.07 | 0.16 | 42.2 |

For instance, $VO_2$ nano-rods perform with 11% efficiency improvement when placed on the present micro-chip (from $\eta=36.5$ to $\eta=47.5$) whereas carbon nanotubes improve from $\eta=8.5$ to $\eta=42.2$ which is 34% efficiency improvement. This means practically any sensing material can now sense at room temperature with this invention.

The invention not only displays better performance but shows the fastest sensing and fastest recovery over and above what is in literature so far.

The efficiency improvement also comes with an added feature of selectivity improvement. This is incorporated in the design by having the gate where the voltage polarity and magnitude can both be used to tune the device to be sensitivity to only certain gases and to "shut off" other gases.

The ease of placing nano-materials on the device is another important advantage of this invention.

Figure 8:
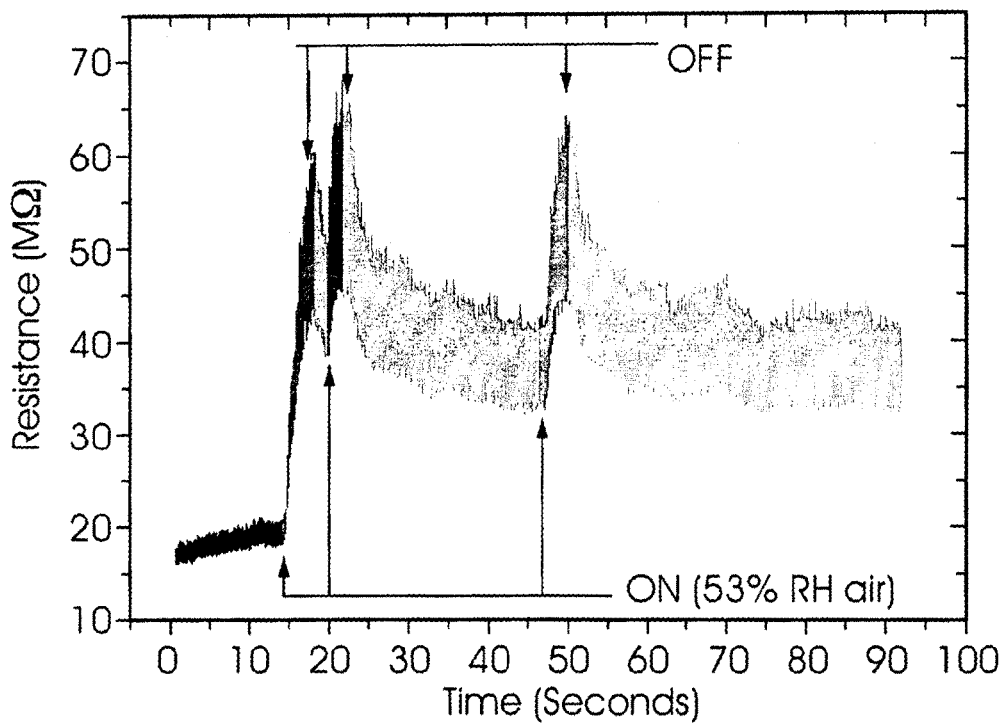
FIG. 8 shows the resistance across the VO2/V2O5 core shell nano-ribbons in time in normal air and when they are exposed to humid air, the response times are typically 5 seconds whereas recovery times are in the order of minutes.
Figure 9:
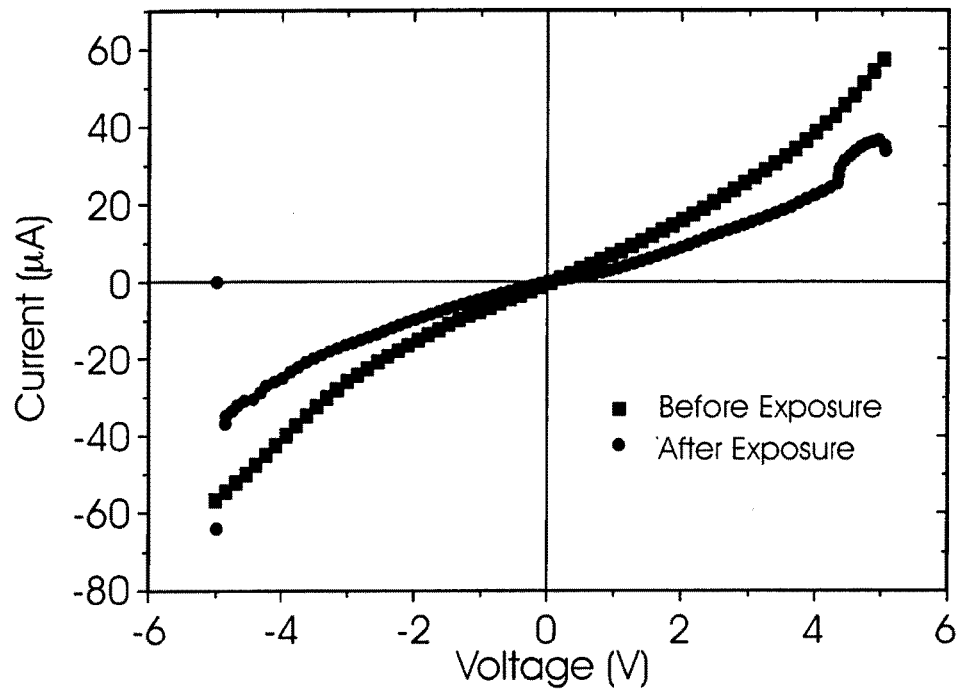
FIG. 9 shows forward current-voltage (Id versus Vds) characteristics for the MWCNT fibre in normal conditions and after being exposed to humid air.
Figure 10:
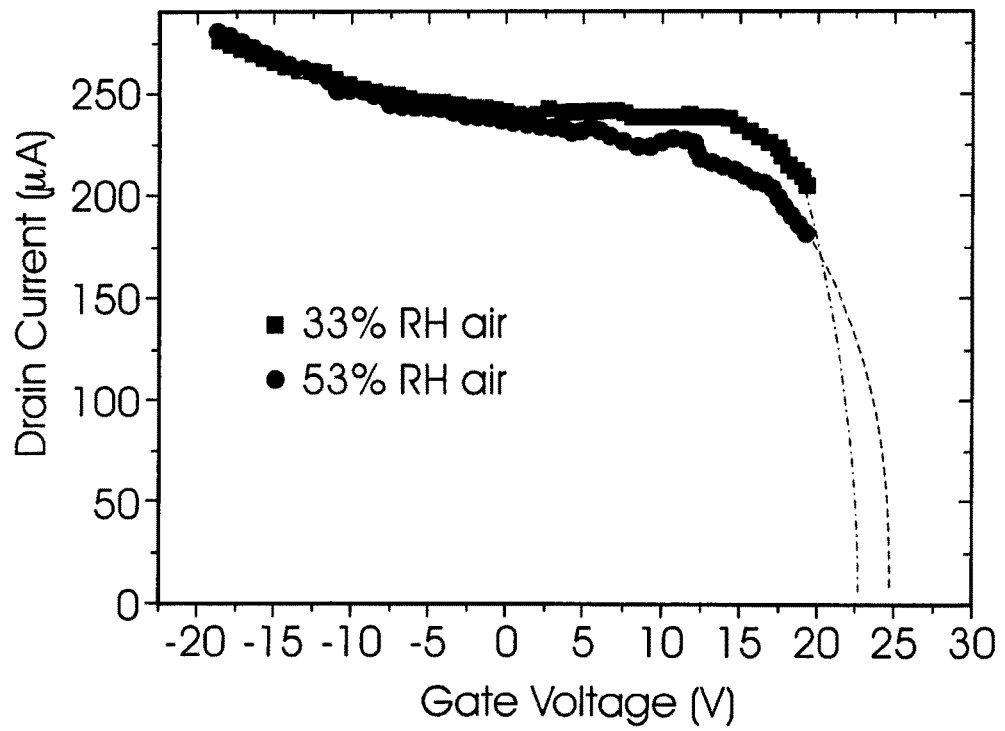
FIG. 10 shows drain current plotted against gate voltage when the CNT chip is in normal air and under the influence of humid air.

In a prototype of the present invention, the detector was used to detect and quantify the following gases which are typically emitted in the mines, Methane ($CH_4$), radon (Rn), and industrial-related pollution such as ammonia ($NH_3$), nitrogen oxides (NOx), carbon monoxide (CO) and silane ($SiH_4$) as shown in FIG. 8(e) where the $VO_2/V_2O_5$ FET sensors display to be more selective to $NH_3$ than the other gases.

An innovative aspect of the present invention is the ability to use the gate voltage as the "tuning" variable of the FET sensor. In accordance with Equations 3 and 4, the drain-source current is affected greatly by the gate voltage as in traditional FETs but, here, the drain current experiences reversal in direction (negative conductance/resistance) when the gate voltage exceed a characteristic threshold voltage (VT). This behavior is novel in FETs and this is ascribed to the geometry of the interdigitate drain source area and the gate. An added feature is the ability to display a hump in the plot of response versus gate voltage. This hump appears at a characteristic gate voltage for each material on the FET sensor as well as for each stimulus. This has been tried before with backgate FETs [2,3] where finally the research failed to show that the traditional backgate transistor could show the same critical gate voltage regardless of the concentration of the stimulating gas.

However in the present invention, regardless of the concentration of acetone or level of humidity, both the VO2/V2O5 and CNT FET sensor show the repeatedly the same critical gate voltage for a particular gas. These humps are in agreement with Equation 6 above. This will be a turning point in the sensing industry across the globe where selectivity of nano-materials has been the weakest link.

Figure 16:
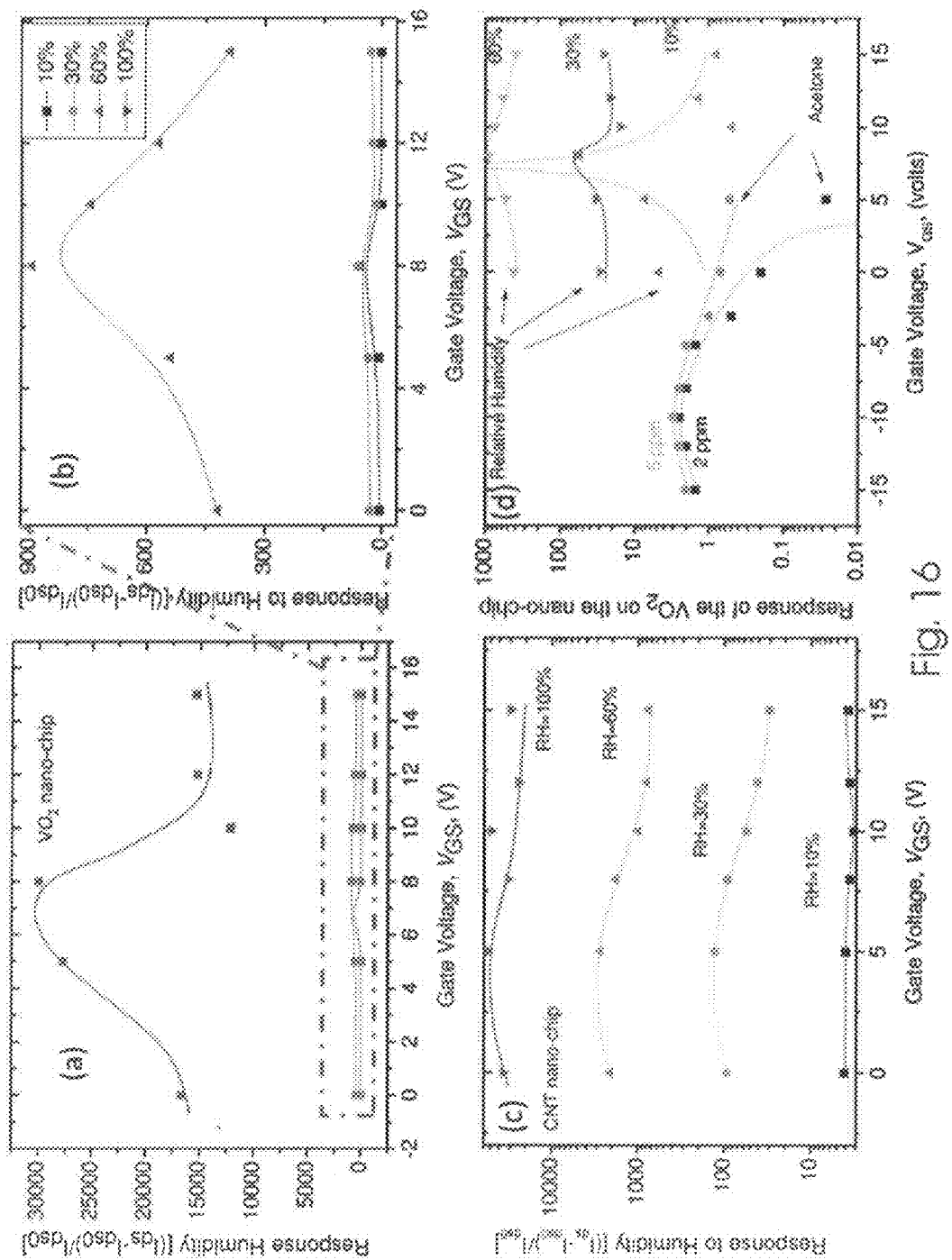
FIG. 16 shows a response to different level of humidity of a typical VO2/V2O5 FET sensor on the chip versus gate voltage.

In FIG. 16(a) is shown the response to different level of humidity of a typical VO2/V2O5 FET sensor on the invented chip versus gate voltage and (b) an zoom-in of the lower humidity lineshapes. In both (a) and (b) there is a characteristic optimum response to humidity at a critical gate voltage of 8 V regardless of the level of humidity, in (c) response to different levels of humidity of one of the eight CNT FET sensors versus gate voltage. In this case the CNT responds to humidity optimally at a critical voltage of 3 V. In (d) is shown response of the one of the eight VO2/V2O5 FET sensors to both humidity and acetone vapor. Acetone, regardless the level of it, shows a peak at VGS=−5V whereas humidity, regardless of the intensity of it, shows a peak at VGS=8 V The detector could also be configured for the following uses:
  Detect breath odor from patients for early detection of diabetes, renal (kidney and liver) failure and ulcers.
  Detection of parts per billion of gas concentrations emitted from TNT and other explosives) from concealed explosives such as land mines and mobile bombs in public places such as airports.
  Control of drug trafficking by detecting gases emitted from the various types of intoxicating drugs such as mandrax, marijuana etc.
  It will be appreciated that the FET described above, being at the nano-scale, allows for room temperature gas detection enabling pollution monitoring without the need of heating the sensors as is common in traditional electronic noses.

FIG. 12 shows an example application of the sensor to diabetes monitoring. The invented sensor response is plotted against glucose concentrations in a patient's blood. It will be appreciated that in the first results, a linear correlation is suggestive between blood sugar and the sensor response.

This shows that the painful finger-pricking ordeal a patient has to undergo more than twice a day with traditional means of monitoring blood glucose can be replaced with the device wherein the patient will simply be required to exhale his/her breath onto the sensor and the same read-out of blood sugar is obtained.

Integration on a single wafer of this kind, that is the traditional heater-based sensors, is not possible with traditional gas sensors which employ a heater for each sensor, as the heat from one spot flows to other parts of the chip.

In traditional gas sensors, the sensing material is heated via printed Pt or CoPt electrodes at the back of the substrate on top of which the sensing material is placed. The need for a heater at the back of the sensor device stems from the observation that each particular gas interacts uniquely and optimally with the sensor material at a specific optimum temperature. The gap between the features on the printed heater can be 150-180 μm. Similarly, the feature size between the electrodes that harness the sensing materials will traditionally have feature sizes of the same order of magnitude as the printed heater.

If one has to place several such devices on one microchip, each device has to be set at its particular temperature for that particular device to be calibrated to a specific gas. It is difficult to place several of such sensing modules in one micro-chip because the heat from one sensor would defuse into other sensor devices if the devices are on a single substrate. In this way, it would be extremely difficult to keep the temperature on a particular device at a desired constant temperature since there would be a lot of thermal cross-talk between the devices and, for this reason, gas specificity has been the most difficult challenge in the contemporary gas sensing community globally.

The new invention removes heating but rather controls the interaction of the one gas with the sensing material via the gate voltage of the field-effect transistor. The feature sizes can now be as small as 1 μm and therefore it is possible now to place eight FET sensing modules in a very small spot without suffering from the said cross-talk.

Figure 13:
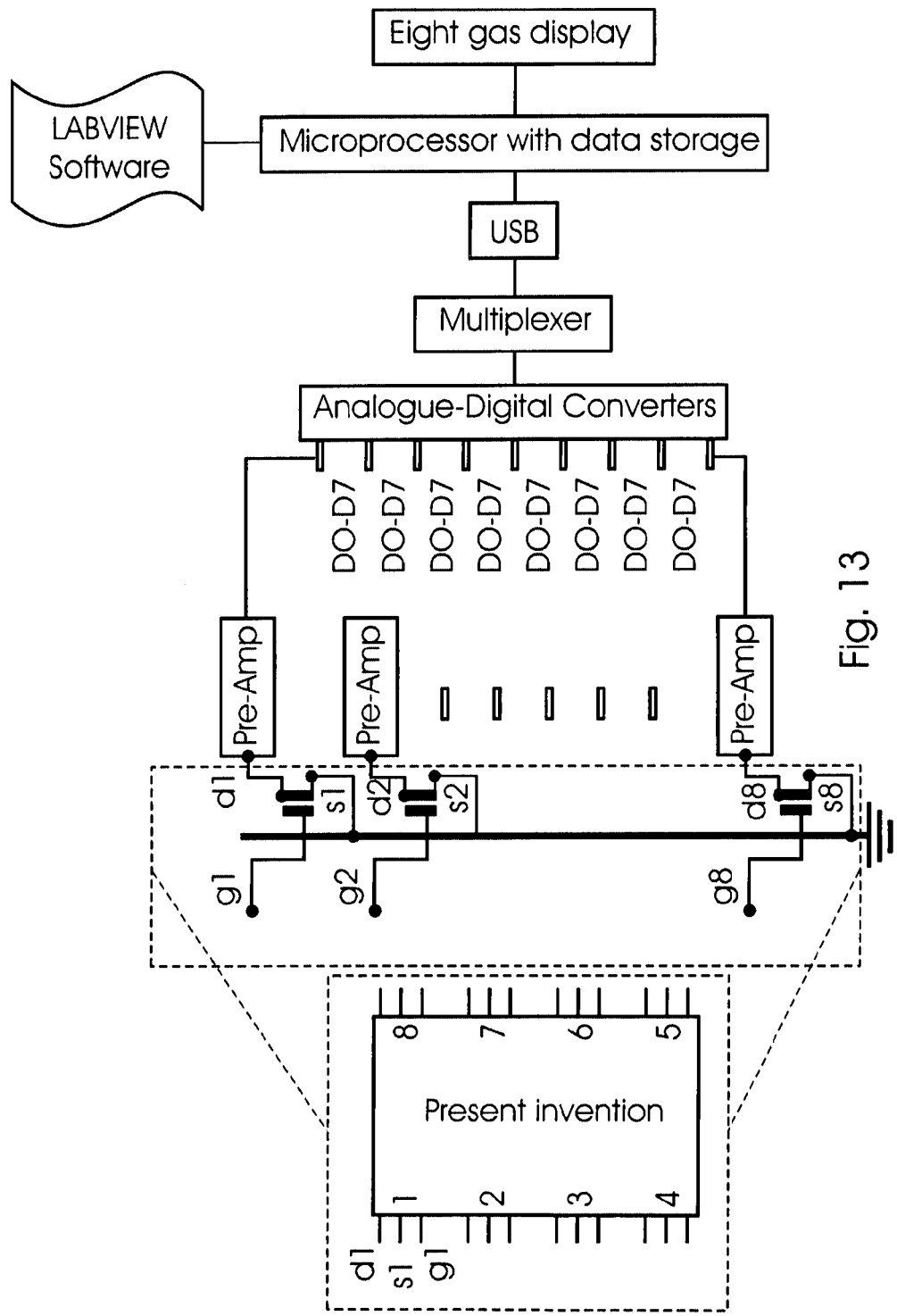
FIG. 13 is a block diagram illustrating how a gas detector may be wired for the detection of up to eight different gases at ambient temperature.

In any event, FIG. 13 shows a schematic of how the invented micro-chip including the plurality of FETs may be inter-connected with electronics featuring interfaces with micro-processor, data storage and display of up to eight different gases.

The signals received from the sensor are amplified and then converted to a digital signal by an analogue to digital converter. The various signals from each of the chips are multiplexed and then via a USB connector, fed into a computer including software operating that processes the signals received and allows them to be displayed, stored and manipulated.

Thus the processor receives signals from each of the field effect transistors and processes the signals to determine the presence of one or more gases.

It will be appreciated that the size of the micro-chip makes it possible to integrate with modern devices like cell phones receivers and other memory devices It will also be appreciated that in the present invention, there is no contact between the gate and the drain-source. This yields new FET properties.

Random placement of nano-particles between the drain-source allows for tuning of the channel-to-gate length (CGL) which is a new parameter to FETs Such LGNFETs are integrated onto a single 1 mm by 1 mm Si/SiO2 wafer making this micro-chip one of the smallest areas so far to contain up to eight (8) sensing elements.

Each FET can be calibrated to sense one particular gas type making this chip a 1 mm-square-eight-gas detector.

FIG. 14(a) shows forward current-voltage characteristics for VO2/V2O5 core-shell nano-ribbons in normal conditions for different levels of gate voltage. In (b) is shown a plot of ID versus VGS. Note the reversal in drain current when VGS becomes greater than VT. In (c-d) are shown drain current versus time as one of the eight VO2/V2O5 FET sensor are exposed to humid air of various relative humidity levels and as gate voltage (VGS) is varied from 0 to 15V. In (e) are shown typical responses of VO2 to various gases (CO, CH4, NO2, NH3 and H2S) and the preferential selectivity to NH3. In (f) are shown resistance of the drain-source channel versus time as the gate voltages are varied from −5V to 5V. Note the rapid recovery when the sensor is biased with a gate voltage of −5V. More analysis of these data are displayed in FIG. 16.

Figure 15:
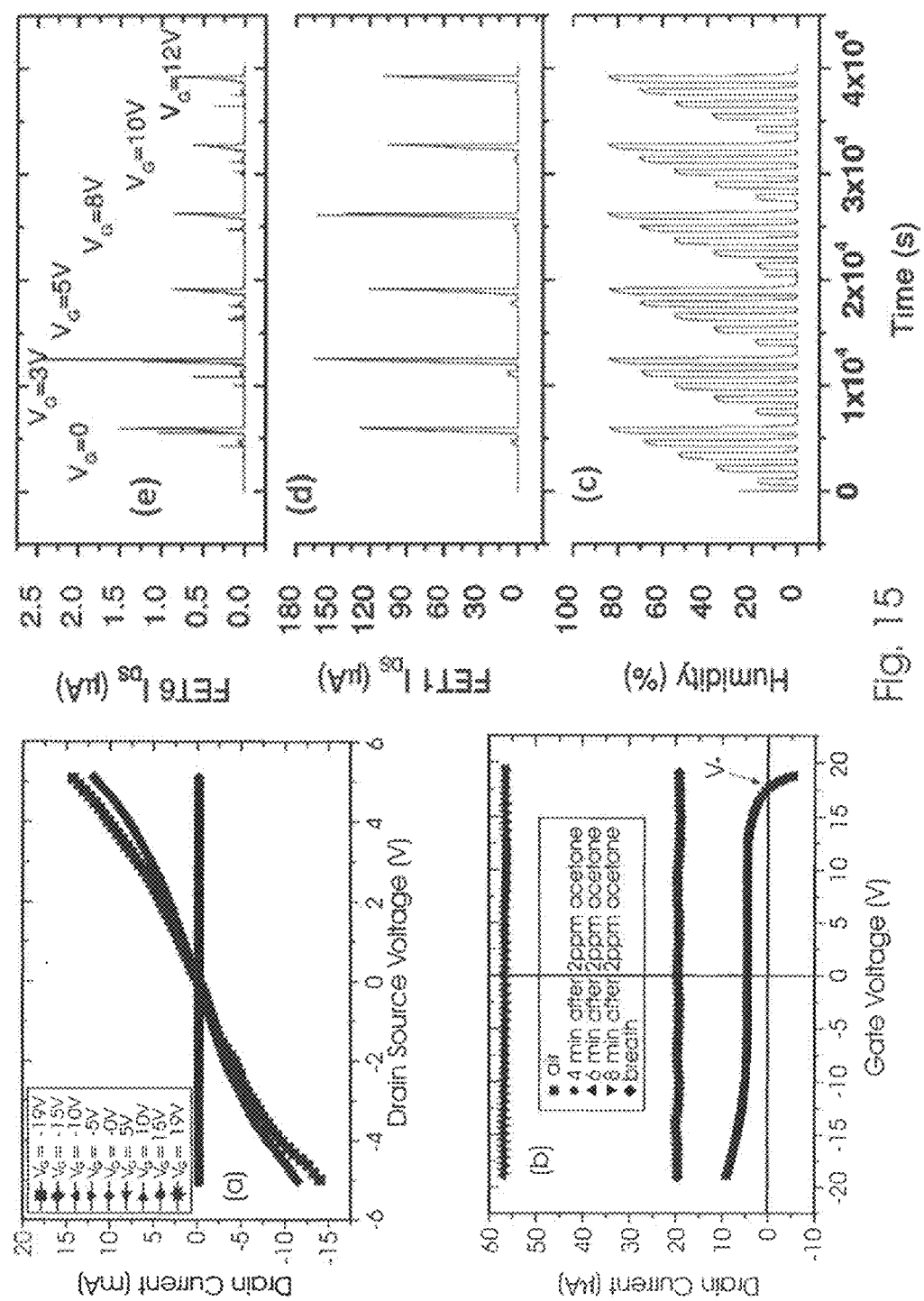
FIG. 15 shows forward current-voltage (ID versus VDS) characteristics for the MWCNT fibre.

FIG. 15 shows (a) forward current-voltage (ID versus VDS) characteristics for the MWCNT fibre (FET1) in normal conditions (b) ID vs VGS at a VDS=5V of FET1 in normal atmospheris conditions and after being exposed to humid air and acetone vapour; (c-d) drain current vs time for FET 1 and FET 6 on the micro-nanochip in the presence of humid air (c) at various gate voltage showing the increase and decrease in response to humidity as the gate voltage is increased from 0 to 12V. The maximum response shows at a VGS of 3-5V beyond which the humidity response deceases.

FIG. 16(a) Response to different level of humidity of a typical VO2/V2O5 FET sensor on the chip versus gate voltage and (b) a zoom-in of the lower humidity line shapes. In both (a) and (b) there is a characteristic optimum response to humidity at a critical gate voltage of 8 V regardless of the level of humidity (c) response to different levels of humidity of one of the eight CNT FET sensors versus gate voltage. In this case the CNT responds to humidity optimally at a critical voltage of 3 V. In (d) is shown response of the one of the eight VO2/V2O5 FET sensors to both humidity and acetone vapor. Acetone, regardless the level of it, shows a peak at VGS=−5V whereas humidity, regardless of the intensity of it, shows a peak at VGS=8

Figure 17:
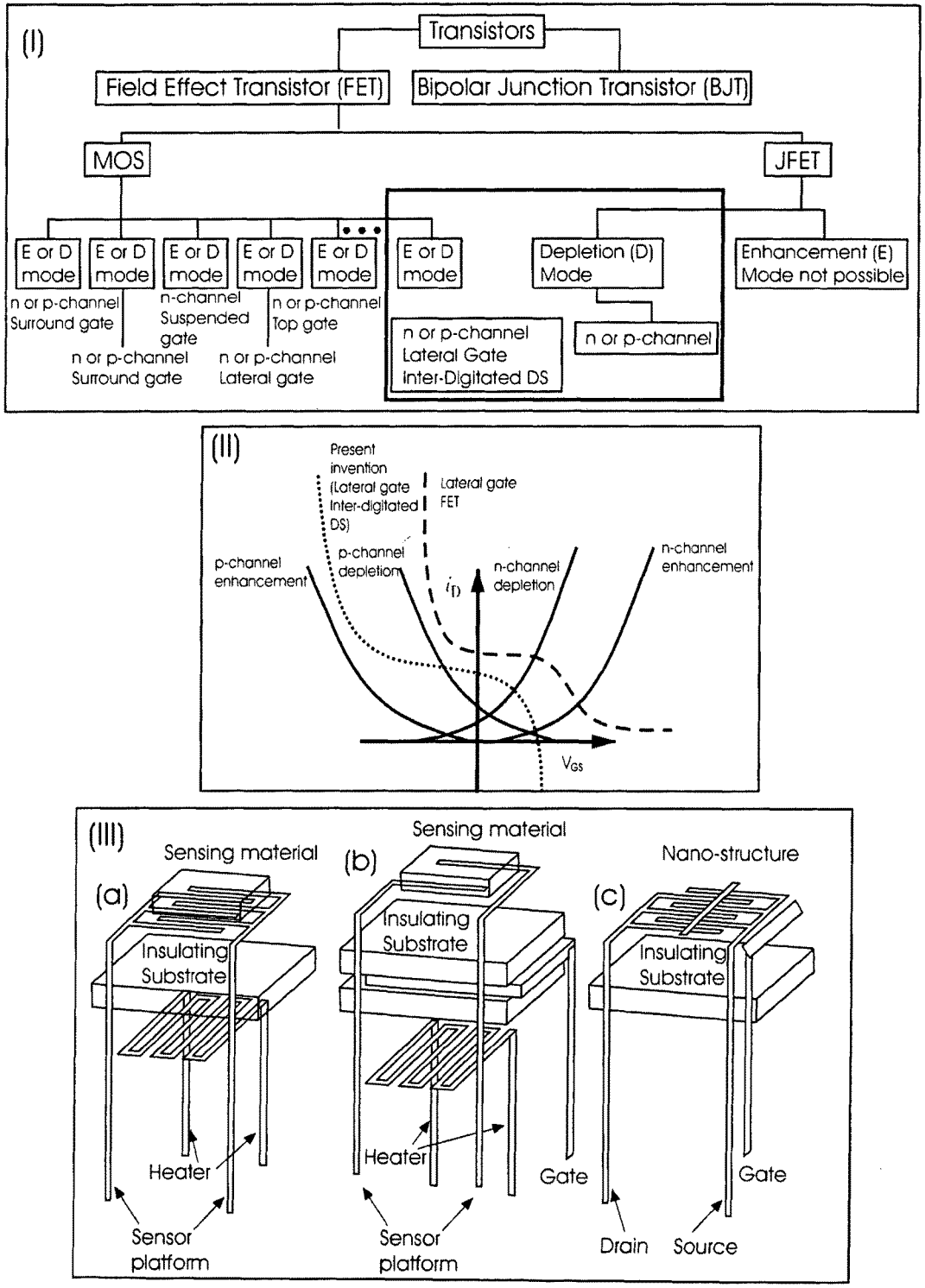
FIG. 17 shows a family tree of all transistors and highlights where in this family the present invention is located.

FIG. 17 (I) shows a family tree of all transistors and highlights where in this family the present invention is located (II) Some distinguishing current-voltage characteristics of the present invention against traditional transitors. (III) Exploded schematic diagrams showing (a) a traditional hot-plate underneath an interdigitated platform whereupon the sensing materials are placed (b) a traditional gasFET showing a gate electrode added and our present heater-less gasFET. Note the difficulty and many processes in designing and implementing schematic (b). However our present design in (c) not only yields new FET properties but also it is an easier design to implement as well as easier to introduce the active sensing material than the traditional gasFET in (b).

APPENDIX A

[1] Bonex Mwakikunga, Sarah Motshekga, Lucky Sikhwivhilu, Mathew Moodley, Gerald Malgas, Manfred Scriba, Suprakas Sinha-Ray, A classification and ranking system on H2 gas sensing capabilities of nano-materials based on proposed coefficients of sensor performance and sensor efficiency equations, Sensors & Actuators B 184 (2013) 170-178

[2] Chao Li, Daihua Zhang, Xiaolei Liu, Song Han, Tao Tang, Jie Han, and Chongwu Zhou, In2O3 nanowires as chemical sensors, Applied Physic Letters 82 (2003) 1613-1615

[3] Daihua Zhang, Zuqin Liu, Chao Li, Tao Tang, Xiaolei Liu, Song Han, Bo Lei, and Chongwu Zhou, "Detection of NO2 down to ppb Levels Using Individual and Multiple In2O3 Nanowire Devices, NANO LETTERS 2004 Vol. 4, No. 10 1919-1924

[4] Arash Dehzangi, A Makarimi Abdullah, Farhad Larki, Sabar D Hutagalung, Elias B Saion, Mohd N Hamidon, Jumiah Hassan and Yadollah Gharayebi, Electrical property comparison and charge transmission in p-type double gate and single gate junctionless accumulation transistor fabricated by AFM nanolithography, Nanoscale Research Letters 2012, 7:381

[5] Farhad Larki, Arash Dehzangi, E. B. Saion, Sabar D. Hutagalung, A. Makarimi Abdullah, M. N. Hamidon, Study of carrier velocity of lateral gate p-type silicon nanowire transistor (PSNWT), Solid State Science and Technology Letter, Vol. 17 No. 1 (2012)

[6] Farhad Larki, Sabar D. Hutagalung, Arash Dehzangi, E. B. Saion, Alam Abedini, A. Makarimi Abdullah, M. N. Hamidon, Jumiah Hassan, Electronic Transport Properties of Junctionless Lateral Gate Silicon Nanowire Transistor Fabricated by Atomic Force Microscope Nanolithography, Microelectronics and Solid State Electronics 2012, 1(1): 15-20

[7] J. Martinez, R. V. Martinez, and R. Garcia, Silicon Nanowire Transistors with a Channel Width of 4 nm Fabricated by Atomic Force Microscope Nanolithography, NANO LETTERS 2008 Vol. 8, No. 11 3636-3639

[8] Bonex Mwakikunga, Suprakas Sihna Ray, Malose Mokwena, John Dewar, Irina Giebelhaus, Trilok Singh, Thomas Fischer, Sanjay Mathur, Tin dioxide nano-wire device for sensing kinetics of acetone and ethanol towards diabetes monitoring, IEEE Sensors Xplore 2013

[9] Bonex Mwakikunga, Suprakas Sihna Ray, Malose Mokwena, John Dewar, Irina Giebelhaus, Trilok Singh, Thomas Fischer, Sanjay Mathur, IEEE Sensors Journal (2014)

[10] Heng Yuan, Bo Wang, Se-Hyuk Yeom, Dae-Hyuk Kwon, Shin-Won Kang, Room temperature benzene gas detection using gated lateral BJT with assembled solvatochromic dye, IMCS 2012—The 14th International Meeting on Chemical Sensors.

The invention claimed is:

1. A field effect transistor comprising:
    a source including a plurality of electrode projections with spaces in between;
    a drain including a plurality of electrode projections each located in one of the spaces between the electrode projections of the source thereby forming a drain-source electrode connection area of alternating drain and source projections;
    a gate spaced apart from the drain-source electrode area thereby forming a channel between the gate and the drain-source electrode connection area wherein the gate runs parallel to the channel; and
    a plurality of nano-structures located in the drain-source electrode area thereby to form an electrical connection between the electrode projections of the drain and source in the drain-source electrode connection area;
    wherein the drain, source and the gate are in the same plane.

2. A field effect transistor according to claim 1 wherein the electrode projections of the drain are elongate in shape and connected at or near one of their ends.

3. A field effect transistor according to claim 1 wherein the electrode projections of the source are elongate in shape and connected at or near one of their ends.

4. A field effect transistor according to claim 1 wherein the plurality of nano-structures located in the drain-source electrode area are positioned randomly on the drain-source electrode area.

5. A field effect transistor according to claim 1 wherein the drain-source electrode connection area is approximately 90 micron by 90 micron.

6. A gas detector including a plurality of field effect transistors located on a substrate, each of the field effect transistors including:
    a source including a plurality of electrode projections with spaces in between;
    a drain including a plurality of electrode projections each located in one of the spaces between the electrode projections of the source thereby forming a drain-source electrode connection area of alternating drain and source projections;
    a gate spaced apart from the drain-source electrode area thereby forming a channel between the gate and the drain-source electrode connection area wherein the gate runs parallel to the channel; and
    a plurality of nano-structures located in the drain-source electrode area thereby to form an electrical connection between the electrode projections of the drain and source in the drain-source electrode connection area;
    wherein the drain, source and the gate are in the same plane.

7. A gas detector according to claim 6 including eight field effect transistors located on a substrate.

8. A gas detector according to claim 6 wherein the gas detector includes a processor to receive signals from each of the field effect transistors and to process the signals to determine the presence of one or more gases.

* * * * *